(12) United States Patent
Schaefer et al.

(10) Patent No.: US 9,162,962 B2
(45) Date of Patent: Oct. 20, 2015

(54) PROCESS FOR RECLAIMING METHACRYLIC ACID FROM A HIGH-BOILER PHASE AND AN AQUEOUS PHASE

(75) Inventors: Henning Schaefer, Darmstadt (DE); Torsten Balduf, Pfungstadt (DE); Patrick Peter, Darmstadt (DE)

(73) Assignee: Evonik Röhm GmbH, Darmstadt (DE)

( * ) Notice: Subject to any disclaimer, the term of this patent is extended or adjusted under 35 U.S.C. 154(b) by 0 days.

(21) Appl. No.: 14/342,116

(22) PCT Filed: Sep. 16, 2011

(86) PCT No.: PCT/CN2011/079775
§ 371 (c)(1),
(2), (4) Date: Feb. 28, 2014

(87) PCT Pub. No.: WO2013/037135
PCT Pub. Date: Mar. 21, 2013

(65) Prior Publication Data
US 2014/0221687 A1    Aug. 7, 2014

(51) Int. Cl.
*C07C 51/48* (2006.01)

(52) U.S. Cl.
CPC ...................................... *C07C 51/48* (2013.01)

(58) Field of Classification Search
CPC ....................................................... C07C 51/48
USPC ......................................................... 562/600
See application file for complete search history.

(56) References Cited

U.S. PATENT DOCUMENTS

| | | | |
|---|---|---|---|
| 6,051,736 A | 4/2000 | Schraut et al. | |
| 2005/0054874 A1 | 3/2005 | Yada et al. | |
| 2010/0120949 A1 | 5/2010 | Balduf | |
| 2010/0130648 A1 | 5/2010 | Balduf | |

FOREIGN PATENT DOCUMENTS

| | | | |
|---|---|---|---|
| CA | 2 282 492 A1 | | 9/1998 |
| JP | 62-153242 | | 7/1987 |
| JP | 06086400 B | * | 11/1994 |
| JP | 2001-514643 | | 9/2001 |
| JP | 2002-128728 | | 5/2002 |
| WO | 98/40342 | | 9/1998 |

OTHER PUBLICATIONS

U.S. Appl. No. 14/342,116, filed Feb. 28, 2014, Schaefer, et al.
U.S. Appl. No. 14/240,547, filed Feb. 24, 2014, Balduf, et al.
U.S. Appl. No. 14/129,811, filed Dec. 27, 2013, Koestner, et al.
International Search Report issued Jun. 28, 2012 in PCT/CN2011/079775 filed Sep. 16, 2011.
Written Opinion of the International Searching Authority issued Jun. 28, 2012 in PCT/CN2011/079775 filed Sep. 16, 2011.
Office Action issued Mar. 2, 2015 in Saudi Arabia Patent Application No. 112330844 (with English language translation).
Japanese Office Action dated Jun. 22, 2015, in corresponding application No. 2014-530069 with English translation.

* cited by examiner

*Primary Examiner* — Yong Chu
(74) *Attorney, Agent, or Firm* — Oblon, McClelland, Maier & Neustadt, L.L.P.

(57) ABSTRACT

The invention relates to a process for reclaiming methacrylic acid from a high-boiler phase in a heterogeneously catalysed gas phase oxidation of a C4-compound to methacrylic acid comprising the following steps a) Providing a high-boiler phase from a heterogeneously catalysed gas phase oxidation of a C4-compound to methacrylic acid b) Providing an aqueous phase, preferably organically loaded, from a heterogeneously catalysed gas phase oxidation of a C4-compound to methacrylic acid c) Mixing of components a) and b) optionally followed by filtration or centrifugation d) Adding an extraction media to the mixture from c) e) Subjecting the multiple-phase mixture from d) to at least one mixer-settler extraction process f) Recycling the organic phase from the last mixer-settler process back into the C4-process

15 Claims, 2 Drawing Sheets

US 9,162,962 B2

PROCESS FOR RECLAIMING METHACRYLIC ACID FROM A HIGH-BOILER PHASE AND AN AQUEOUS PHASE

CROSS REFERENCE TO RELATED APPLICATIONS

The present application is a 35 U.S.C. §371 national stage patent application of International patent application PCT/CN2011/079775, filed on Sep. 16, 2011, published as WO/2013/037135 on Mar. 21, 2013, the text of which is incorporated by reference.

The invention relates to a process for reclaiming methacrylic acid from a high-boiler phase and an aqueous phase.

Methacrylic acid (MAA) is used in a wide variety of applications. The commercial production of methacrylic acid occurs, among other ways, by heterogeneously catalysed gas phase oxidation of isobutylene, tert-butanol, methacrolein or isobutyl aldehyde. The thus obtained, gaseous reaction phase is transformed into an aqueous methacrylic acid solution by cooling and condensing, optionally separated from low-boiling substances such as, for example, acetaldehyde, acetone, acetic acid, acrolein and methacrolein and then introduced into a solvent extraction column, in order to extract and separate methacrylic acid by means of suitable extraction agents, such as, for example, short-chain hydrocarbons. The separated methacrylic acid is further purified, for example by distillation, to separate high-boiling impurities, such as, for example, benzoic acid, maleic acid and terephthalic acid, in order to obtain a pure methacrylic acid. Such a known process is described for example in EP 0 710 643, U.S. Pat. Nos. 4,618,709, 4,956,493, EP 386 117 and U.S. Pat. No. 5,248,819.

Such known processes generate large amounts of waste water at various process stages, of which the greatest amount is in the form of the aqueous phase remaining after the extraction of the methacrylic acid from the quench phase. The water comes mainly from added steam or water into the gas phase oxidation step, and from the use of water as quenching agent in the cooling and condensing step, as well as from the oxidation reaction itself. This waste water contains considerable amounts of organic compounds and cannot be reused or safely disposed of without further treatment to remove at least partially these organic compounds. Such organic compounds generally include desirable products such as methacrylic acid, due to incomplete extraction into the organic extraction agent, as well as other byproducts of the oxidation step such as acrylic acid, acetic acid and propionic acid, which also have commercial value. The organics content in this waste water is generally too high to be compatible with water treatment processes such as biological treatment, for example activated sludge processes, without requiring significant dilution, considerable time and very large treatment facilities, so that in commercial methacrylic acid production the waste water is often combusted, as described, for example, in U.S. Pat. No. 4,618,709. Combustion of waste water is, however, both environmentally and economically unfavourable, requiring high energy input, leading to emissions which may require further treatment before release into the environment, and also leading to loss of potentially valuable organic compounds present in the waste water, as well as loss of the water itself.

It would thus be advantageous to be able to recover at least partially the organic compounds present in the waste water. It would also be advantageous to recover at least some of the water itself, either with an organics content which is sufficiently low for it to be subjected to a biological treatment and/or be discharged into the environment, or in a purity which is sufficient for the water to be reusable, for example as industrial process water or in the methacrylic acid/methyl methacrylate production process itself. CN 1903738 proposes the use of a membrane separator followed by a rectification tower for purifying waste water from acrylic acid production and recovering acrylic acid, toluene and acetic acid. A disadvantage of membrane filtration is that in general large amounts of water—often the waste water itself is used—are required to wash away the components which do not pass through the filter. This washing water with increased concentration of organic compounds must then itself be either further treated or combusted.

Furthermore, various process steps, in particular the generally distillative separation of the methacrylic acid from the extraction agent following extraction of methacrylic acid out of the aqueous quench phase, result in formation of a methacrylic acid phase as distillate and a high-boiler phase as residue—sometimes referred to as bottom phase, as distillation residue or as waste oil—which still contains significant amounts of methacrylic acid. It would be advantageous to be able to recover at least some of this methacrylic acid from the high-boiler phase. Various methods have been suggested for treatment of such high-boiler phases.

EP 1 043 302 proposes a treatment of waste oil from acrylic acid or methacrylic acid production with a solvent, to prevent polymerisation of the waste oil and/or generation of precipitates in the waste oil. US 2005/0054874 discloses, in an acrylic acid or methacrylic acid synthesis, classifying high-boiling heavy ingredients discharged from individual steps by their acrylic or methacrylic acid content, and treating them by combining them with high boiling phases from other industrial processes, so that they can be stored without precipitation of solids. There is, however, no teaching in either of these documents of recovering methacrylic acid from the waste oil.

An object of the present invention is generally to overcome as far as possible the disadvantages of the prior art processes.

A further object is to increase the overall yield of the methacrylic acid and/or methyl methacrylate production process by recovering methacrylic acid from high-boiler phases.

Another object of the present invention is to recover water from the process waste water by reducing as far as possible the contamination of this waste water with organic compounds so that the water can be reused, subjected to a biological purification process, or discharged to the environment, optionally after a biological or other type of purification process.

A contribution to solving the above objects is made by a process for reclaiming methacrylic acid from a high-boiler phase and an aqueous phase, comprising process steps:

a) Providing a high-boiler phase from a heterogeneously catalysed gas phase oxidation of a C4 compound to methacrylic acid b) Providing waste water, preferably organically loaded, from a heterogeneously catalysed gas phase oxidation of a C4 compound to methacrylic acid c) Mixing of components a) and b) optionally followed by filtration or centrifugation d) Adding an extraction media to the mixture from c)

e) Subjecting the multiple-phase mixture from d) to at least one mixer-settler extraction process f) Recycling the organic phase from the last mixer-settler process back into the C4-process.

The C4 compound of the process according to the invention is preferably a C4 compound selected from isobutylene, tert-butyl alcohol, isobutylaldehyde and methacrolein, or a mixture of two or more thereof. In a preferred aspect of the invention, the C4 compound is derived from splitting of methyl tert-butyl ether (MTBE) or ethyl tert-butyl ether (ETBE).

The gas phase oxidation of the process according to the invention preferably occurs in the presence of at least one oxidation catalyst. If the C4 compound is isobutylene or tert-butyl alcohol, the gas phase oxidation to obtain a methacrylic acid-comprising gas phase can occur in one step, whereby one step in this context is considered to mean that initial oxidation to methacrolein and further oxidation to methacrylic acid occur substantially in the same reaction area, in the presence of at least one catalyst. Alternatively, the gas phase oxidation can occur in more than one step, preferably in two steps, preferably in two or more reaction areas separated from each other, whereby two or more catalysts are preferably present, each catalyst preferably being present in a separate reaction area from each other catalyst. In a two-step gas phase oxidation, the first step is preferably at least partial oxidation of the C4 compound to methacrolein, followed by at least partial oxidation of methacrolein to methacrylic acid. Accordingly, for example, in a first reaction step, preferably at least one catalyst suitable for oxidation of at least one C4 compound to methacrolein is present, and in a second reaction step, at least one catalyst suitable for oxidation of methacrolein to methacrylic acid is present.

Suitable reaction conditions for gas phase catalytic oxidation are, for example, temperatures of from about 250° C. to about 450° C., preferably from about 250° C. to about 390° C. and pressures of from about 1 atm. to about 5 atm. The space velocity can vary from about 100 to about 6000 per hr (NTP) and preferably from about 500 to about 3000 per hr. Oxidation, for example gas phase catalytic oxidation, of $C_4$ feeds such as isobutylene to methacrolein and/or methacrylic acid, as well as catalysts therefore, are well known in the literature, for example from U.S. Pat. Nos. 5,248,819, 5,231,226, 5,276,178, 6,596,901, 4,652,673, 6,498,270, 5,198,579, 5,583,084.

Particularly preferred catalysts and processes suitable for oxidation of isobutylene or tert-butanol to methacrolein and/or methacrylic acid are described in EP 0 267 556, and particularly preferred catalysts and processes suitable for oxidation of methacrolein to methacrylic acid are described in EP 0 376 117. These documents are hereby introduced as reference and form part of the disclosure of the present invention.

The gas phase oxidation of methacrolein to methacrylic acid in the process according to the invention preferably occurs at temperatures of from about 250 to about 350° C. and below, at pressures from about 1 to about 3 atm, and at volume loads of from about 800 to about 1800 Nl/l/h.

As oxidising agent, generally oxygen is used, for example, in the form of air, or in the form of pure oxygen or oxygen diluted with at least one gas which is inert under the reaction conditions, such as at least one of nitrogen, carbon monoxide and carbon dioxide, whereby air is preferred as oxidising agent and nitrogen and/or carbon dioxide are preferred as diluent gas. If carbon dioxide is used as diluent gas, this is preferably carbon dioxide recycled from a combustion, preferably a catalytic or thermal combustion of reaction gases and/or byproducts. The gas subjected to gas phase oxidation of the process according to the invention preferably also comprises water, which is generally present in the form of water vapour. The oxygen, inert gas or gases and water can be introduced into the reaction phase or combined with the C4 compound before or during or before and during the gas phase reaction.

In a two-step gas phase oxidation according to the invention, a preferred volume ratio in the first step of C4 compound : $O_2$:$H_2O$ :inert gas is generally 1 : 0.5-5:1-20:3-30, preferably 1 : 1 -3:2-10:7-20. The volume ratio in the second step of methacrolein : $O_2$:$H_2O$:inert gas is preferably 1 : 1 -5:2-20:3-30, preferably 1 : 1-4:3-10:7-18.

In the following step the gas phase which comprises methacrylic acid is cooled and condensed—commonly known as quenching—to obtain a condensate in the form of a crude aqueous methacrylic acid-comprising solution. The condensation can occur by any means known to the skilled person and appearing suitable, for example by cooling the methacrylic acid-comprising gas phase to temperatures below the dew point of at least one of its components, in particular of at least one of water and methacrylic acid. Suitable methods of cooling are known to the skilled person, for example, cooling by means of at least one heat exchanger, or by quenching, for example by spraying the gas phase with a liquid, for example with water, an aqueous composition or an organic solvent, such as, for example, an organic solvent selected from aromatic or aliphatic hydrocarbons, or a mixture of at least two thereof, whereby preferred organic solvents have relatively low vapour pressure under the quenching conditions, such as heptane, toluene or xylene, whereby water is preferred as quench liquid according to the invention, and at least a portion of the condensate formed in the quenching step itself is even more preferred. Suitable quenching processes are known to the skilled person, for example from DE 21 36 396, EP 297 445, EP 297 788, JP 01193240, JP 01242547, JP 01006233, U.S. Pat. Nos. 2001/0007043, 6,596,901, 4,956,493, 4,618, 709, 5,248,819, whose disclosure concerning quenching of acrylic and methacrylic acids is hereby incorporated and forms part of the present disclosure. It is preferred according to the invention that the gas phase is cooled to temperatures between 40 and 80° C. and washed with water and/or condensate from the quenching step to obtain an aqueous solution comprising methacrylic acid, which can also comprise varying amounts of impurities such as acetic acid, maleic acid, fumaric acid, citraconic acid, acrylic acid and formic acid, as well as aldehydes such as formaldehyde, acetaldehyde, propionaldehyde, acrolein, methacrolein, ketones and unreacted C4 compound or compounds. These impurities, as well as water, need to be separated to the greatest extent possible from the methacrylic acid in order to obtain a high degree of purity of methacrylic acid.

The extraction of at least a part of the methacrylic acid from the crude aqueous methacrylic acid-comprising solution occurs in a subsequent process step by means of an organic extraction agent, for example at least one organic solvent, preferably at least one organic solvent which is substantially immiscible with water, such that an aqueous phase and an organic phase can be formed. This process step also comprises the separation of the aqueous and organic phases from each other. Preferred organic solvents have a boiling point different to, preferably lower than, the boiling point of methacrylic acid. Preferably the organic extraction agent has a boiling point of less than 161° C. measured at atmospheric pressure. The organic extraction agent can then in principle be separated from methacrylic acid, for example by distillation, preferably at least partially, preferably to a substantial extent in a following step of the process according to the invention, where it is preferably at least partially removed as a low boiler at a higher level in the distillation apparatus than the pure methacrylic acid. The separated organic extraction agent or a part thereof can be conducted back to process, optionally after at least one cooling and/or purification step. Preferred organic solvents for this step are in particular selected from alkanes and aromatic, preferably alkylaromatic, hydrocarbons, whereby at least one organic solvent selected from a $C_6$-$C_8$ hydrocarbon is preferred, whereby heptane, toluene and xylene are particularly preferred and heptane, preferably n-heptane is most preferred. The extraction and separation process step can be carried out by any means known and appearing suitable to the skilled person, preferably as a countercurrent extraction, for example by means of a solvent extraction column, a pulsed fill or packing column, rotating extractors, a washing column, a phase separator or other device suitable for extraction of an aqueous phase with an organic solvent and separation of the organic phase from the aqueous phase. It is preferred according to the invention that at least a part of the methacrylic acid comprised in the aqueous methacrylic acid solution is extracted into the organic phase.

Two phases are thus obtained: a crude organic phase comprising methacrylic acid and the first aqueous phase comprising any organic compounds which are formed during the gas phase oxidation reaction, such as those mentioned above in connection with the crude aqueous phase obtained in the quenching step, as well as unreacted C4 compounds and any methacrylic acid which has remained in the aqueous phase. This aqueous phase constitutes the preferably organically loaded waste water as defined in process step b).

In a following step the crude organic phase comprising methacrylic acid is subjected to a separation, preferably a thermal separation process to separate at least a part of the methacrylic acid comprised therein from the organic solvent. If a thermal separation is used, this is preferably a distillation, whereby the organic solvent preferably is removed as head product or at an upper level of a distillation column while methacrylic acid or a methacrylic acid-rich phase is removed at a lower level of the distillation column than the extraction solvent. The bottom product in the column, whereby the term "bottom product" also encompasses any phases collected at lower levels of the distillation column than the level or levels at which methacrylic acid phase or phases are collected, is considered as the high-boiler phase according to process step a) of the invention. This bottom product generally comprises components with higher boiling point than methacrylic acid, as well as polymeric materials, together with varying amounts of methacrylic acid, whereby the amount of methacrylic acid can reach up to about 95 wt. % or even more or at least 30 wt. % of the total weight of the high-boiler phase. It is also possible to use, for example, a fractionating or rectification column, so that impurities with boiling points higher than methacrylic acid remain in the bottom product and methacrylic acid of higher purity can be removed at a level of the column which is higher than that of the bottom product. In this case, the methacrylic acid content of the bottom product (high-boiler phase) can be lower than with a simple distillation column.

The high-boiler phase can comprise up to about 95 wt. %, preferably from about 60 wt. % to about 95 wt. %, more preferably from about 65 wt. % to about 90 wt. %, more preferably from about 70 wt. % to about 85 wt. % methacrylic acid, based on the total weight of the high-boiler phase, with the remaining weight of the high-boiler phase being made up of components with higher boiling points than that of methacrylic acid ("high-boilers"), for example high boiling acids such as citraconic acid, maleic acid, terephthalic acid, trimellitic acid and the like, aldehydes such as p-tolualdehyde and benzaldehyde, polymeric materials, in particular polymers of methacrylic acid, as well as polymerisation inhibitors such as, for example, hydroquinone, hydroquinone monomethyl ether, phenothiazine, benzophenothiazine.

In process step c) according to the invention at least a part, preferably at least 50 wt. %, more preferably at least 60 wt. %, more preferably at least 70 wt. %, yet more preferably at least 80 wt. %, even more preferably at least 90 wt. %, more preferably at least 95 wt. %, yet more preferably all of the high-boiler phase obtained according to process step a) of the invention is introduced to the first aqueous phase obtained according to process step b) of the invention. The ratio of high-boiler phase to first aqueous phase can range from 1:10 to 10:1, preferred 2:5 to 5:2, more preferred 3:4 to 4:3 and most preferred 1:1. In this way, the high-boiler phase can be treated together with the first aqueous phase and at least a part of the methacrylic acid comprised in the high-boiler phase can be recovered. A small amount of precipitation can occur on combining the first aqueous phase with the high-boiler phase, so that an optional solid-liquid separation such as filtration or centrifugation can be carried out, if necessary, for example, if the amount of precipitate is sufficient to negatively influence one or more further process steps, or to interfere with transport of the liquid phase, in particular through pipes, before conducting the one or more liquid phases to further process steps.

The combined phases a) and b) are now combined with a suitable organic solvent as extraction media in process step d) and introduced into a first mixer-settler extraction process, process step e) according to the invention. Preferred organic solvents for this process step d) are in particular selected from alkanes and aromatic, preferably alkylaromatic, hydrocarbons, whereby at least one organic solvent selected from a $C_6$-$C_8$ hydrocarbon is preferred, whereby heptane, toluene and xylene are particularly preferred and heptane, preferably n-heptane is most preferred. The ratio of the combined high-boiler phase/aqueous phase (feed) to extration media can range from 1:10 to 10:1, preferred 2:5 to 5:2, more preferred 3:4 to 4:3 and most preferred 1:1.

Mixer-settler processes are known to those skilled in the art. Mixer-settlers generally consist of single or several stages in series, each stage consisting of a stirred vessel and a settling vessel. Various arrangements are possible such as concurrent, countercurrent, or crosswise flow of phases. Stage efficiencies of nearly 100% can be achieved and mixer-settlers are almost insensitive to load fluctuations. Backmixing can be completely avoided due to complete phase separation in each stage. As a result, there are generally no transfer problems in scale-up. The favorable efficiency is almost completely retained even for large throughputs. Any number of separation stages can be built, and throughput does not appear to be limited. Examples are described in Ullmann's Encyclopedia of Industrial Chemistry, 5th Edition, Wiley-VCH, Weinheim, Vol. B3, Chapter 6, "Liquid-Liquid Extraction". Optionally there can be several mixer-settler processes in sequence, in a preferred embodiment of the invention there are three mixer-settler devices in line, most preferred are two. It is preferred according to the invention that the mixer-settler extraction processes are carried out continuously.

After the last mixer-settler unit, the organic phase is recycled back according to process step f) of the invention to one of the solvent-methacrylic acid separation columns mentioned above, while the aqueous phase is introduced to a waste water treatment plant or to a thermal oxidizer.

REFERENCE SIGNS

B-100/-200 Vessel
HS High-boiler phase
WW Waste water, first aqueous phase
P-100/-200 Pumps
WT 100 Heat exchanger
R-310 Static mixer
R-320 Stirred mixer
B-330 Settler
B-410/-420 Vessel
WI-410/-420 Weight scales
T1360/T1380 Solvent recovery columns within C4-process
Q1-Q10 Sampling points
TO Thermal oxidizer

EXAMPLES

Figure 1:
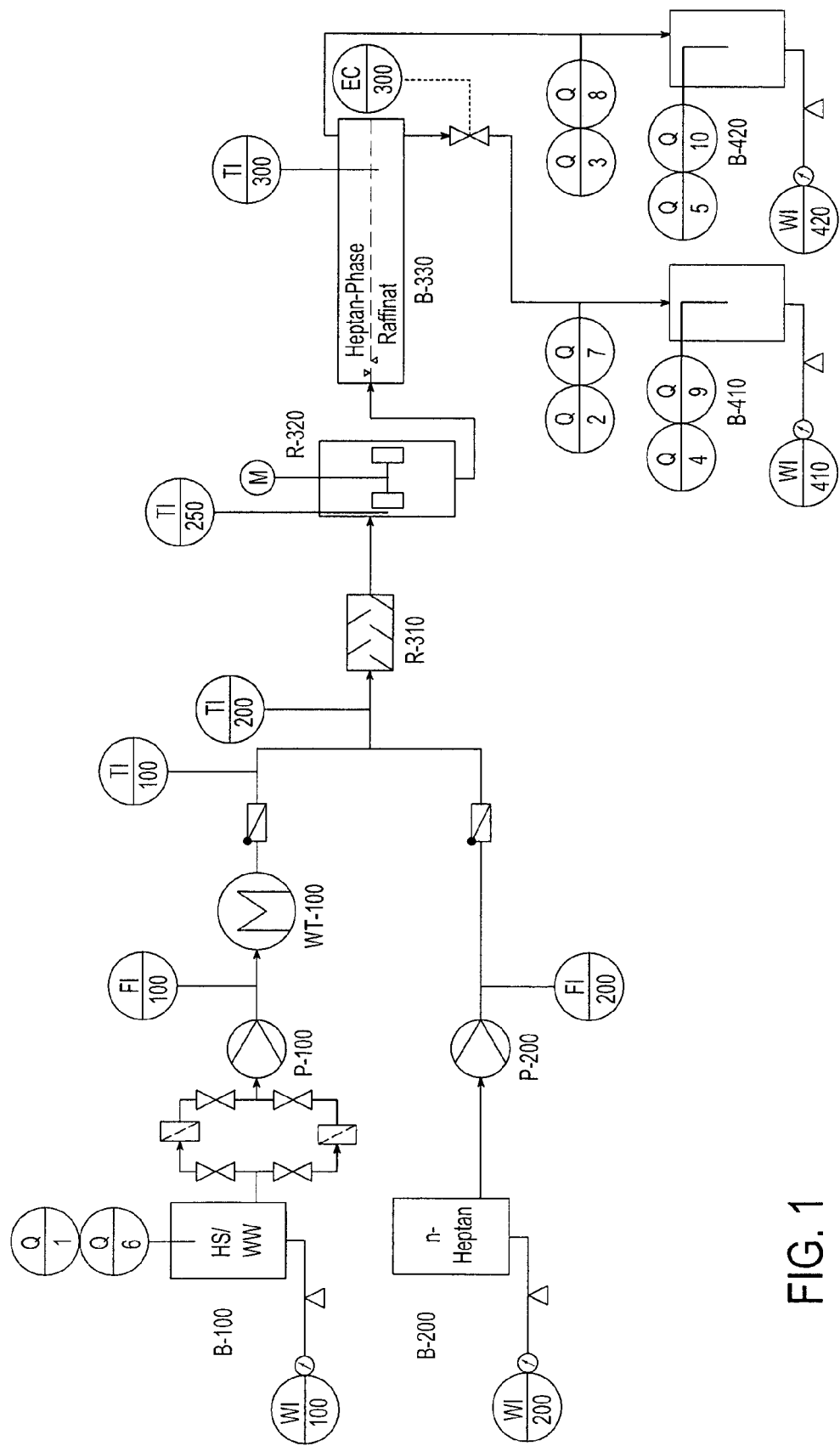
FIG. 1 shows the experimental setup.
Figure 2:
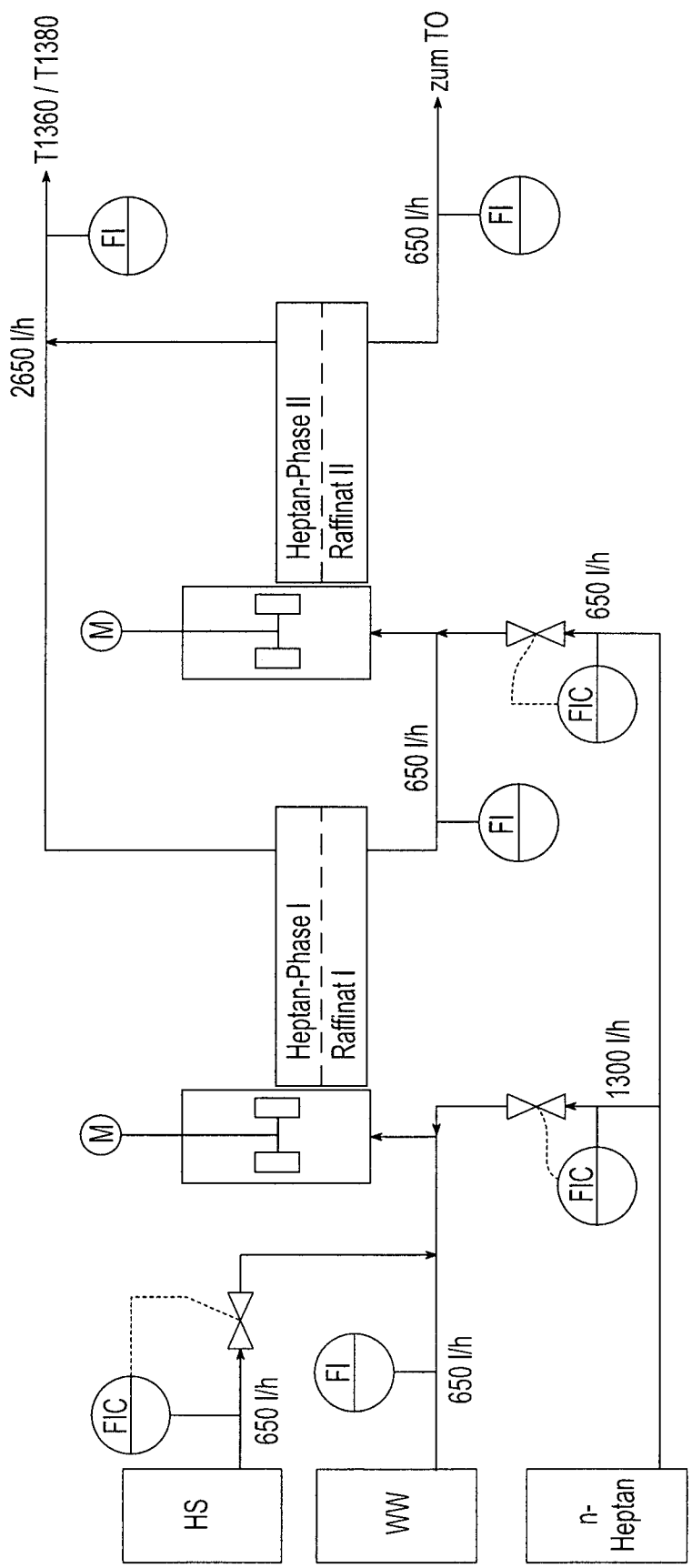
FIG. 2 illustrates an example of the process steps c)-e) according to the invention but does not limit the invention to any extent.

Examples 1-6 were carried out in an apparatus according to FIG. 1. The different ratios of high-boiler phase and aqueous phase were combined and passed through a paper filter. The filtrate was used as a feed to the continuous mixer-settler setup. The feed was preheated in the heat exchanger WT-100, mixed with different amounts of n-heptane (see table of results) as extraction media and passed through a static mixer (R-310). Within the mixer (R-320) intensive mixing of the high-boiler/aqueous phase and n-heptane is accomplished, while in the settler (B-330) the phases separate. When equilibrium is reached, analytical samples are extracted at points Q1-Q3, at the end of the run at Q4-Q6. Since this continuous experimental setup realizes only one separation step, each run was carried out long enough (about 16 h) to collect enough feed for the next extraction step. The mixer-settler setup was run exclusively in the crosswise-flow mode.
Results:

|  | Ratio |  |  |  |  | Partition Coefficients |  |  |  |  |  |  |  |  |
|---|---|---|---|---|---|---|---|---|---|---|---|---|---|---|
|  | High Boiler | Aqueous Phase | Ratio Feed | Ratio Heptane | Temp. °C. | Extraction | n-Heptane | Acetone | Water | Acetic Acid | AA | MAA | Benzoic Acid | 4-Methyl Benzoic Acid | MAA-Yield |
| Example 1 | 1 | 0.5 | 1 | 1 | 50 | stage 1 | 115.95 | 0.00 | 0.03 | 0.08 | 0.90 | 0.65 | 0.75 | 0.79 | 48.40% |
|  | 1 | 0.5 | 1 | 1 | 50 | stage 2 | 189.68 | 0.00 | 0.02 | 0.06 | 0.55 | 0.51 | 0.53 | 0.62 | 66.00% |
|  | 1 | 0.5 | 1 | 1 | 50 | stage 3 | 213.20 | 0.00 | 0.02 | 0.03 | 0.28 | 0.40 | 0.40 | 0.46 | 73.40% |
| Example 2 | 1 | 0.5 | 1 | 1.5 | 50 | stage 1 | 89.15 | 0.00 | 0.03 | 0.05 | 1.80 | 0.60 | 0.50 | 0.59 | 55.00% |
|  | 1 | 0.5 | 1 | 1.5 | 50 | stage 2 | 242.78 |  | 0.02 | 0.03 | 0.29 | 0.45 | 0.39 | 0.49 | 69.70% |
|  | 1 | 0.5 | 1 | 1.5 | 50 | stage 3 | 133.39 | 0.18 | 0.02 | 0.02 | 0.00 | 0.32 | 0.28 | 0.00 | 74.60% |
| Example 3 | 1 | 0.5 | 1 | 2 | 50 | stage 1 | 104.44 | 0.00 | 0.02 | 0.05 | 1.90 | 0.58 | 0.53 | 0.71 | 61.40% |
|  | 1 | 0.5 | 1 | 2 | 50 | stage 2 | 215.48 |  | 0.02 | 0.04 | 0.38 | 0.39 | 0.34 | 0.46 | 76.10% |
|  | 1 | 0.5 | 1 | 2 | 50 | stage 3 | 31.69 | 0.00 | 0.02 | 0.02 | 0.00 | 0.27 | 0.24 | 0.00 | 79.60% |
| Example 4 | 1 | 1 | 1 | 1 | 20 | stage 1 | 450.29 | 0.00 | 0.01 | 0.11 | 0.40 | 1.32 | 1.44 | 2.63 | 70.30% |
|  | 1 | 1 | 1 | 1 | 20 | stage 2 | 1502.83 | 0.00 | 0.01 | 0.06 | 0.20 | 1.03 | 1.35 | 3.06 | 84.50% |
|  | 1 | 1 | 1 | 1 | 20 | stage 3 | 537.28 | 0.00 | 0.01 | 0.04 | 0.00 | 0.72 | 1.09 | 1.29 | 89.30% |
| Example 5 | 1 | 1 | 1 | 1.5 | 20 | stage 1 | 1007.50 | 0.00 | 0.01 | 0.09 | 0.32 | 1.25 | 1.37 | 2.33 | 76.70% |
|  | 1 | 1 | 1 | 1.5 | 20 | stage 2 | 9311.00 | 0.00 | 0.01 | 0.04 | 0.00 | 0.86 | 1.08 | 3.88 | 89.00% |
|  | 1 | 1 | 1 | 1.5 | 20 | stage 3 | 627.17 | 0.00 | 0.01 | 0.01 | 0.02 | 0.00 | 0.56 | 0.67 | 92.40% |
| Example 6 | 1 | 1 | 1 | 2 | 20 | stage 1 | 1696.20 | 0.00 | 0.01 | 0.08 | 0.23 | 1.21 | 1.42 | 2.89 | 80.20% |
|  | 1 | 1 | 1 | 2 | 20 | stage 2 | 4794.00 | 0.00 | 0.01 | 0.04 | 0.00 | 0.72 | 1.00 | 1.83 | 91.20% |
|  | 1 | 1 | 1 | 2 | 20 | stage 3 | 4833.50 | 0.00 | 0.01 | 0.02 | 0.00 | 0.38 | 0.41 | 0.00 | 93.80% |

The MAA partition coefficient increases with increasing aqueous phase ratio, the influence of increasing heptane ratio is negligible. Best increase of MAA yield is observed between stage 1 and stage 2.

The invention claimed is:

1. A process for reclaiming methacrylic acid from a high-boiler phase and an aqueous phase in a heterogeneously catalyzed gas phase oxidation of a C4-compound to methacrylic acid, the process comprising:
   mixing (i) a high-boiler phase obtained from a heterogeneously catalyzed gas phase oxidation of a C4-compound to methacrylic acid, with (ii) an aqueous phase obtained from a heterogeneously catalyzed gas phase oxidation of a C4-compound to methacrylic acid, to obtain a mixture;
   optionally filtering or centrifuging the mixture;
   adding an organic solvent to the mixture, to obtain a multiple-phase mixture;
   performing at least one mixer-settler extraction process on the multiple-phase mixture, to obtain an organic phase and; and
   recycling an organic phase from the last mixer-settler process back into the oxidation of the C4-compound to the metharcrylic acid,
   wherein the C4-compound is selected from the group consisting of isobutylene, tert-butyl alcohol, isobutylaldehyde and methacrolein.

2. The process of claim 1, wherein the high-boiler phase comprises at least 30 wt. % of methacrylic acid.

3. The process of claim 1, wherein a weight ratio of the high-boiler phase to the aqueous phase is from 10:1 to 1:10.

4. The process of claim 1, wherein a weight ratio of the high-boiler phase/aqueous phase to the organic solvent is from 10:1 to 1:10.

5. The process of claim 1, wherein the mixer-settler extraction process is carried out at a temperature of 10-60° C.

6. The process of claim 1, wherein the mixer-settler extraction process is carried out continuously.

7. The process of claim 1, wherein the filtering is performed.

8. The process of claim 1, wherein the centrifuging is performed.

9. The process of claim 1, wherein both the filtering and the centrifuging are performed.

10. The process of claim 1, comprising performing more than one mixer-settler extraction process.

11. The process of claim 10, wherein each mixer-settler extraction process is carried out at a temperature within the range of 10-60° C.

12. The process of claim 10, wherein each mixer-settler extraction process is carried out continuously.

13. The process of claim 1, wherein the aqueous phase is organically loaded.

14. The process of claim 1, wherein the organic solvent is a $C_6$-$C_8$ hydrocarbon.

15. The process of claim, wherein the organic solvent is at least one selected from the group consisting of heptane, toluene and xylene.

* * * * *